US00PP08715P

United States Patent [19]

Hill, Jr.

[11] Patent Number: Plant 8,715

[45] Date of Patent: May 3, 1994

[54] GUZMANIA PLANT NAMED GUINN

[75] Inventor: Herbert H. Hill, Jr., Lithia, Fla.

[73] Assignee: Twyford International, Inc., Santa Paula, Calif.

[21] Appl. No.: 17,669

[22] Filed: Feb. 10, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new cultivar of Guzmania named Guinn having bright red bract color which is not affected by heat, short and compact habit, a good tolerance to hard water, white flower bracts, and bracts which are relatively wide and extend more horizontally to provide a wide flowering structure.

1 Drawing Sheet

The present invention comprises a new and distinct cultivar of Guzmania, botanically known as *Guzmania hybrida,* and referred to by the cultivar name Guinn. The new cultivar is a product of a planned breeding program carried out by the inventor Herbert Henry Hill, Jr. in Lithia, Fla. The cultivar was discovered by him from the progeny of the stated cross. The male parent is an unnamed cultivar of *Guzmania lingulata,* and the female parent is a likewise unnamed cultivar of *Guzmania wittmackii.* Both parents are publicly available.

Asexual propagation by division was performed in Lithia, Fla. by the inventor to increase the number of plants for evaluation, and such propagation has clearly demonstrated the stability of the combination of characteristics of Guinn from generation to generation.

The following observations, measurements and values describe plants grown in Lithia, Fla. under greenhouse conditions which closely approximate those generally used in horticultural practice.

The following traits have been repeatedly observed to be characteristics which in combination distinguish Guinn from other Guzmania of the same general type, including the well known cultivars Cherry and Grand Prix, to which reference is made.

1. Guinn is shorter and more compact than Cherry or Grand Prix.

2. Guinn's bract color is not affected by high growing temperatures while Cherry becomes more orange.

3. Guinn has more red color on the scape bracts than Cherry or Grand Prix, resulting in a brighter blooming structure.

4. Guinn is more tolerant of hard water than Cherry or Grand Prix.

5. Guinn's bracts extend more horizontally than Cherry, making a wider flowering structure.

6. Guinn has white flower bracts while Cherry has yellow flower bracts.

7. Guinn has wider bracts than Grand Prix.

All color references are measured against The Royal Horticultural Society Colour Chart. Colors, and sizes and amounts of inflorescence parts are approximate as they depend on horticultural practices such as light level, temperature, fertilization rate and age, among others.

The accompanying color photographic drawing shows typical characteristics of Guinn with colors being as true as possible with illustrations of this type.

Origin: Seedling.

Parentage:

*Male parent.*—An unnamed cultivar of *Guzmania lingulata.*

*Female parent.*—An unnamed cultivar of *Guzmania wittmackii.*

Classification: *Guzmania hybrida* cv Guinn.

Propagation: In a 6" pot, Guinn after 65 to 70 weeks under appropriate growing conditions from division reaches a mature size of approximately 30 cm. to 40 cm. in height excluding the inflorescence, approximately 45 cm. to 55 cm. in height including the inflorescence, and approximately 70 to 80 cm. (widest point) in width.

Stem: The stem is approximately 13 cm. to 17 cm. in height and approximately 7 cm. to 8 cm. in width when the plant is in full bloom.

Leaves:

*Form.*—The leaf blade is ligulate having an attenuate tip. The margins are entire along the edge. The midrib tends to droop towards the apex. The leaf blade is relatively thin. The leaf surface is smooth and shiny in appearance.

*Size.*—Leaf blades of a mature sized plant are approximately 53 cm. to 60 cm. in length and approximately 3.3 cm. to 4 cm. in width.

*Color.*—Upper surface, greener than 137A; lower surface, more yellow than 137C.

Inflorescence:

*Form.*—The inflorescence is terminal in origin and pinnate in form. It is approximately 14 cm. to 17 cm. in height from bottom of flower to apex of spike, and approximately 17 cm. to 20 cm. in width.

*Flowers.*—Form: The flowers are sessile and not secund. There are approximately 8 to 12 flowers on each lateral with approximately 11 to 14 lateral spikes and approximately 15 to 19 flowers on the main spike. The reproductive organs are not commercially significant. The new cultivar is not known to set seed. Petals: The petals are approximately 2.5 cm. to 3.5 cm. in length, approximately 0.3 cm. to 0.5 cm. in width, and 3C to 4B in color. Tips are 155A in color. Sepals: The sepals are smooth, linear and have an attenuate apex. They are approximately 2.5 cm. to 3.2 cm. in length and approximately 0.3 cm. to 0.5 cm. in width. They are 155A in color. Ovaries: The ovaries will be approximately 2.5 mm. to 3.5 mm. in diameter at their widest point, are linear and flat in cross section, and are 155A in color.

*Floral bracts.*—The floral bracts have a mucronate apex and are 1C in color. flushed with rose near the tip. They are approximately 3.5 cm. to 5.5 cm. in length and approximately 1 cm. to 2.5 cm. in width.

*Primary bracts.*—The primary bracts are imbricate and have an acuminate apex. They are approximately 15 cm. to 16 cm. (basipetal) and 5 cm. to 6 cm. (acropetal) in length, and approximately 5 cm. to 6 cm. (basipetal) and 2.5 cm. to 3 cm. (acropetal) in width. They are 45C with green tips, with the base (basipetal bracts) being 145A.

Acropetal bracts are 144B, 145A with tips darker than 45C.

*Scape bracts.*—The scape bracts are remote and have an acuminate apex. They are approximately 20 cm. to 24 cm. in length and approximately 4 cm. to 5 cm. in width. They are greener than 137B with rose areas where bract separates from stem in color.

*Scape.*—The scape is approximately 32 cm. to 40 cm. in height, approximately 9 mm. to 11 mm. in diameter, and 150C in color.

Roots: White to brown wiry roots with fine laterals.

I claim:

1. A plant of a new and distinct cultivar of Guzmania plant named Guinn, as illustrated and described.

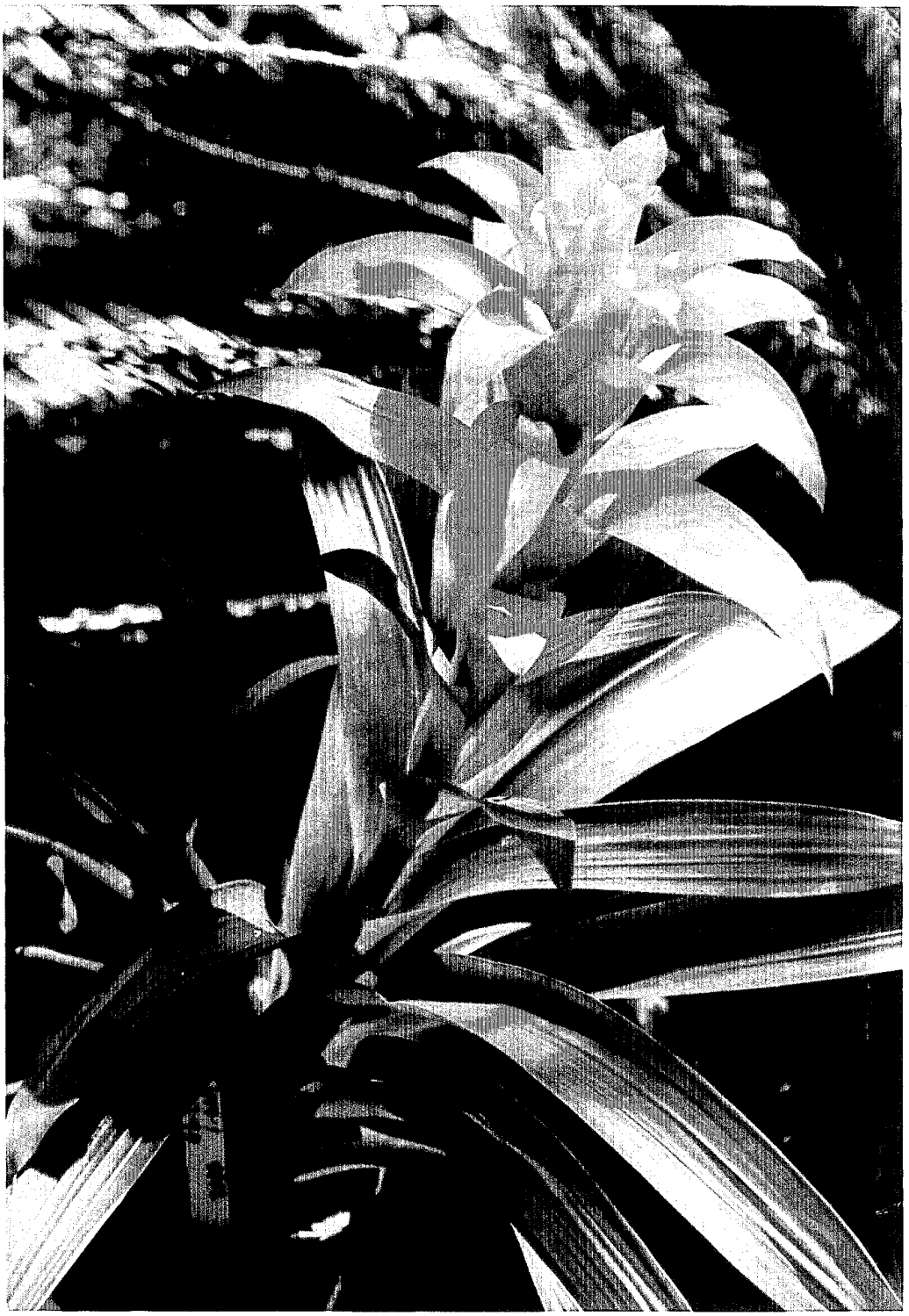

* * * * *